United States Patent [19]

Carlson et al.

[11] Patent Number: 4,476,712
[45] Date of Patent: Oct. 16, 1984

[54] SAMPLING HIGH PURITY WATER FOR TRACE ION DETERMINATION

[75] Inventors: Gerald L. Carlson, Mt. Lebanon Township, Allegheny County; Warren E. Snider, Elizabeth Township, Allegheny County, both of Pa.

[73] Assignee: Westinghouse Electric Corp., Pittsburgh, Pa.

[21] Appl. No.: 64,319

[22] Filed: Aug. 6, 1979

[51] Int. Cl.³ ............................................. G01N 31/08
[52] U.S. Cl. .............................. 73/61.1 C; 73/864.83
[58] Field of Search ...... 73/61.1 C, 422 GC, 422 TC, 73/422 R, 425.6

[56] References Cited

U.S. PATENT DOCUMENTS 3,010,583 11/1961 Kenyon ..................... 73/422 R X
3,442,136 5/1969 Wilson, Jr. ................... 73/422 TC
3,897,679 8/1975 Guild .............................. 73/61.1 C

OTHER PUBLICATIONS

*Determination of Organic Vapors in the Industrial Atmosphere*, In Bulletin 769, Supelco, Inc., pp. 1–5, 1977.

Primary Examiner—S. Clement Swisher
Assistant Examiner—Joseph W. Roskos
Attorney, Agent, or Firm—R. D. Fuerle

[57] ABSTRACT

Apparatus is disclosed for collecting and concentrating trace ions from a pressurized aqueous sample in a sample line. A three-way valve is connected to the sample line which in one position can divert the sample into a syringe and in another position can close off the sample line and permit the sample to flow from the syringe through the three-way valve into a concentrator column. In an alternative apparatus, the sample line is connected to a tee which permits the diversion of the sample into a concentrator column connected to the tee. The other end of the concentrator column is joined to a syringe for drawing the sample through the concentrator column. Methods of operating the apparatus are also disclosed.

8 Claims, 3 Drawing Figures

SAMPLING HIGH PURITY WATER FOR TRACE ION DETERMINATION

BACKGROUND OF THE INVENTION

The detection and quantification of low parts per billion levels of ionic species in water is becoming of increasing importance in a number of processes. For example, in the steam and boiler water used in electrical power plants, ionic species such as sodium, chloride, sulfate, nitrate, phosphate, and potassium can lead to the pitting of turbine blades even when present at only the parts per billion level. In order to analyze for ions present in such minute amounts, a representative sample of the fluid must be collected in a totally inert container and put into a form suitable for the analytical method, avoiding all possibility of contamination. In the case of anions, the sample must be preconcentrated 10 to 100 times in order to bring the sample into the sensitivity range of the best analytical methods. A major problem in analyzing for such low levels of ions is the difficulty in finding an inert container for storing them. Some container materials will contaminate the sample with species leached out of the container walls while other container materials remove trace impurities by irreversible absorption onto the interior surfaces of the container. The storage time required for these sample distortions to occur is largely unknown. Thus, a method for collecting and preconcentrating high purity water samples which avoids the use of containers, minimizes the handling of the sample, concentrates the sample and leaves the concentrated sample in a form compatible with the analytical method to be used would be very desirable.

SUMMARY OF THE INVENTION

We have discovered that trace ions can be collected and concentrated from a pressurized aqueous sample by filling a syringe with the sample then forcing the sample from the syringe through a concentrator column. Alternatively, the sample can flow directly through the concentrator column into a syringe which provides a vacuum for drawing the sample through the column. In this way, the sample does not contact the walls of any container for a prolonged period. The concentrated sample can then be analyzed by ion chromatography.

PRIOR ART

In bulletin 769, entitled, "Determination of Organic Vapors in the Industrial Atmosphere" published in 1977 by Supelco, Inc., charcoal absorption tubes are used for the collection of atmospheric pollutants which are then analyzed by gas chromatography.

DESCRIPTION OF THE INVENTION

Figure 1:
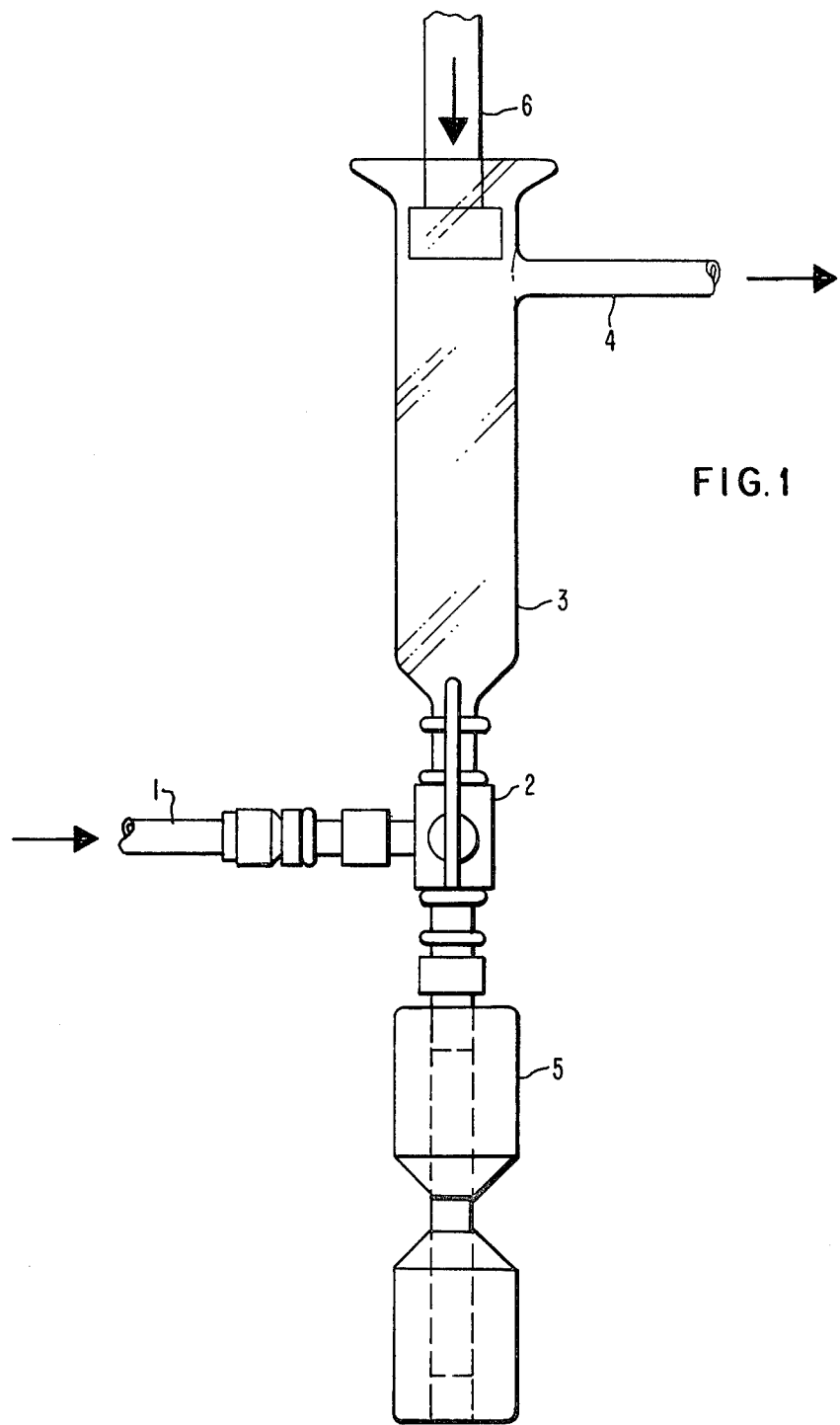
FIG. 1 is a diagrammatic side view of an apparatus for collecting and concentrating trace ions according to this invention.

In FIG. 1, sample line 1, containing a pressurized aqueous sample to be analyzed, is connected to three-way valve 2. The sample flows from line 1 through three-way valve 2 into syringe 3 and out drain 4 of syringe 3, thereby flushing out the syringe. A suitable syringe size for this apparatus is about 10 ml. and about 1 or 2 minutes are required to take a sample. When the syringe has been flushed out, three-way valve 2 is turned to permit flow from syringe 3 into concentrator column 5 which is connected to three-way valve 2. By applying pressure to plunger 6 of syringe 3, a sample of known quantity is forced out of syringe 3 through three-way valve 2 and into concentrator column 5, which concentrates the trace ions present in the sample. Concentrator column 5 contains a suitable resin and a liquid eluant as is known in the art. If anions are being analyzed, the eluant is usually sodium carbonate and water, and if cations are being analyzed the eluant is usually weak hydrochloric acid or nitric acid in water. The concentrator column can then be sealed and taken to a laboratory for analysis, for example, by ion chromatography, or an ion chromatograph can be connected directly to the concentrator column. While other techniques of analysis can also be used, ion chromatography is preferred as it the most sensitive technique.

Figure 2:
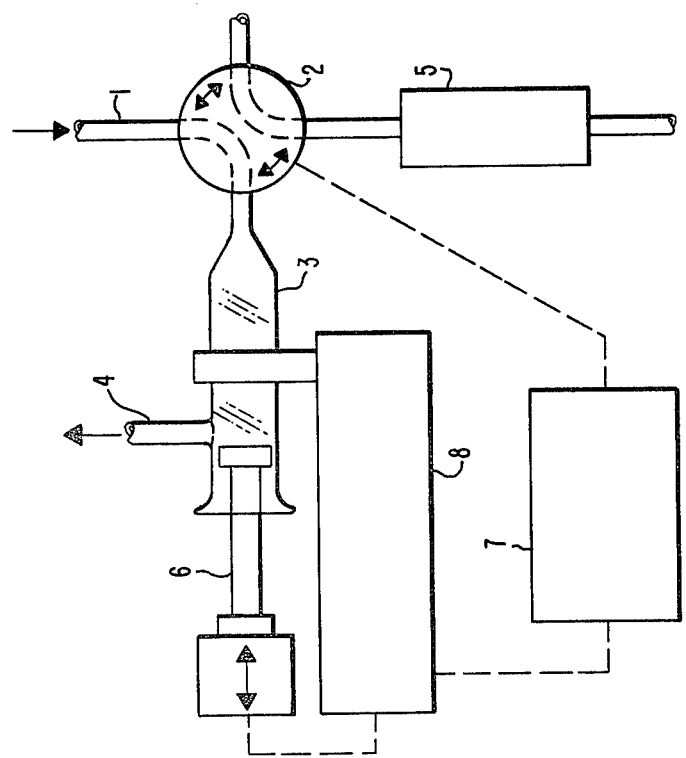
FIG. 2 is a diagrammatic side view of a certain presently preferred embodiment of a portion of FIG. 1.

In FIG. 2, there is shown an alternative apparatus which can be applied to the apparatus of FIG. 1 in order to automate the procedure. In FIG. 2, sample line 1, three-way valve 2, syringe 3, drain 4, and concentrator column 5 are the same as in FIG. 1. However, a timer and pump/valve controller 7 has been added which periodically turns valve 2 so that a sample may be taken and analyzed. After the syringe has been flushed, the controller turns three-way valve 2 so that fluid can flow from syringe 3 into concentrator column 5 and it activates motor driven syringe pump 8 which drives the plunger 6 of syringe 3 forcing fluid in the syringe through three-way valve 2 and into concentrator column 5.

Figure 3:
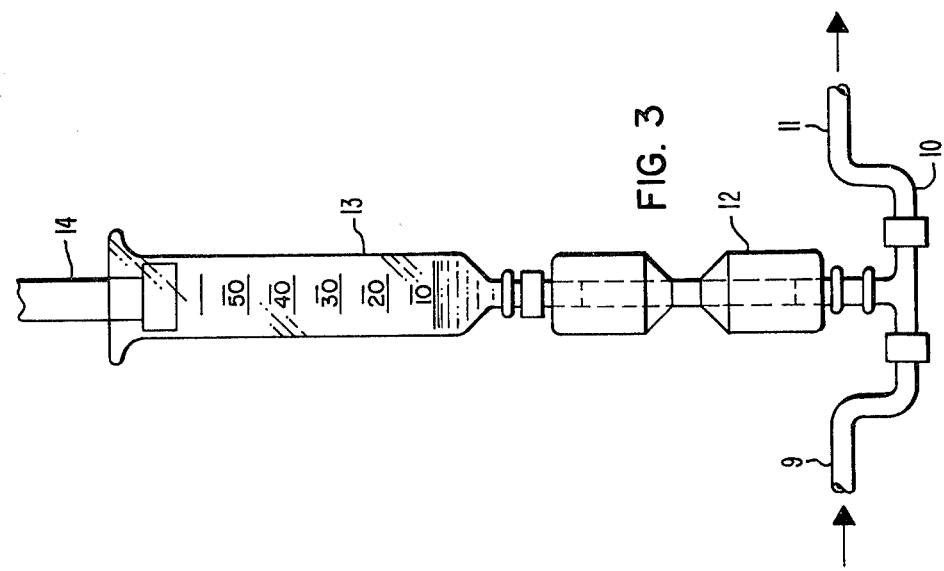
FIG. 3 is a diagrammatic side view of a certain presently preferred embodiment of an apparatus for collecting and concentrating trace ions according to this invention.

In FIG. 3, there is illustrated an alternative apparatus according to this invention. In FIG. 3, sample line 9 is connected to tee 10 so that the sample passes through the tee and into drain 11. The sample can also pass from the tee into concentrator column 12 and then into syringe 13 which is connected to the other end of concentrator column 12. Raising plunger 14 of syringe 13 creates a vacuum within the syringe which draws the sample through the concentrator column and into the syringe. The amount of sample that passes through the concentrator column can then be directly measured with the syringe. The apparatus of FIG. 3 is preferred because a larger quantity of fluid is sampled over a longer time which evens out temporary variations in the impurity levels of the sample. A suitable syringe size for this apparatus is about 50 ml. and about 45 minutes are required to take a sample.

The following example further illustrates this invention.

EXAMPLE

Samples from the water of a turbine operating under a load of 295 mw were collected and concentrated using the apparatus of FIG. 1 or FIG. 3. The samples were subsequently analyzed for sodium, chloride, and sulfate. The following table gives the time that the samples were collected and the results of the analysis. The table shows a high degree of consistency in the analysis using the two types of apparatus.

| Sample Type | Apparatus FIG. # | Time | Na$^{+(a)}$ (ppb) | Cl$^-$ (ppb) | SO$_4^=$ (ppb) |
| --- | --- | --- | --- | --- | --- |
| LP Steam | 1 | 1:25 pm | <1 | <1 | 2 |
| | 3 | 1:20–1:45 | | 1.5 | 0 |
| | 1 | 3:24 | | 1 | 0 |
| | 3 | 3:22–3:52 | | 1.5 | 1 |
| | 3 | 4:05–4:41 | | 1 | 1 |
| | 3 | 4:05–4:50 | | 2 | <1 |
| Condensate | 1 | 2:20 pm | | 3.5 | 4.5 |
| | 3 | 2:25–2:45 | | 4 | 1 |
| Feedwater | 1 | 2:00 pm | <1 | 6.5 | 3 |
| | | 2:00–2:25 | | 5 | 4.5 |
| Make-up$^{(b)}$ | 1 | 2:25 pm | 2.5 | 48 | 1 |
| | 1 | 3:10 | | 45 | <1 |
| Boiler Water$^{(c)}$ | 1 | 2:07 pm | | ~1000 | ~200 |

$^{(a)}$Na$^+$ determination limited because of interference by alkylamine or NH$_4^+$ used for pH control.
$^{(b)}$Cation sample also contained Nh$_4^+$.
$^{(c)}$Boiler water also showed the expected high concentraion PO$_4^\equiv$.

We claim:

1. Apparatus for collecting and concentrating trace ions from a pressurized aqueous sample in a sample line, comprising:
   (A) a three-way valve connected to said sample line;
   (B) a syringe connected to said three-way valve, whereby said sample can flow through said three-way valve into said syringe; and
   (C) a concentrator column connected to said three-way valve whereby said sample can flow from said syringe through said three-way valve into said concentrator column.

2. Apparatus according to claim 1 wherein said syringe includes a drain at the end opposite the entry of said aqueous sample.

3. Apparatus according to claim 1 including an ion chromatograph attached to said concentrator column to analyze said ions after they pass through said column.

4. Apparatus according to claim 1 including a timer, a motor for driving the plunger of said syringe, and means for automatically turning said three-way valve, whereby said timer periodically turns said three-way valve to flush and fill said syringe, turns said three-way valve to permit said aqueous sample to flow from said syringe to said concentrator, and activates said motor to drive the plunger of said syringe.

5. A method of collecting and concentrating trace ions in a pressurized aqueous sample comprising flushing said aqueous sample through a syringe and filling said syringe with said aqueous sample, terminating the flow of said aqueous sample through said syringe, and forcing said aqueous sample from said syringe through a concentrator column, collecting and concentrating said trace ions in said concentrator column.

6. A method according to claim 5 wherein said syringe is flushed through a drain therein.

7. A method according to claim 5 including the additional last step of passing said aqueous sample from said concentrator column through an ion chromatograph to analyze for trace ions therein.

8. A method according to claim 5 wherein said method is periodically and automatically practiced.

* * * * *